United States Patent [19]

Scherr

[11] 4,096,138
[45] Jun. 20, 1978

[54] IMMUNOLOGICAL TEST PROCEDURE

[76] Inventor: George H. Scherr, 50 Monee Rd., Park Forest, Ill. 60466

[21] Appl. No.: 638,548

[22] Filed: Dec. 8, 1975

[51] Int. Cl.$^2$ .......................... A23T 1/06; C07G 7/00
[52] U.S. Cl. ............................... 260/121; 260/112 R; 424/12
[58] Field of Search ........................... 260/112 R, 121

[56] References Cited

U.S. PATENT DOCUMENTS

| | | | |
|---|---|---|---|
| 2,372,066 | 3/1945 | Fell | 260/112 R |
| 3,553,310 | 1/1971 | Csizmas et al. | 260/112 R X |
| 3,690,834 | 9/1972 | Goldstein et al. | 260/112 R X |
| 3,850,752 | 11/1974 | Schuurs et al. | 424/12 X |
| 3,940,475 | 2/1976 | Gross | 424/12 X |
| 3,975,342 | 8/1976 | Gross | 260/121 |

Primary Examiner—Walter C. Danison
Attorney, Agent, or Firm—Kinzer, Plyer, Dorn & McEachran

[57] ABSTRACT

A method is described for conducting immunological tests in which a hapten or antigen is coupled to a soluble macromolecule of natural origin which complex is then aggregated into a particulate suspension which can then be used in an agglutination or indirect agglutination test procedure for detecting antigens or haptens similar in special configuration to that coupled to the macromolecule or detecting antibodies specific for such haptens or antigens. The aggregation for the protein can be affected initially with subsequent coupling of the hapten or antigen to it, or aggregation can be effected after hapten or antigen coupling to the macromolecule.

The test procedure utilizing such aggregate macromolecule-hapten or macromolecule-antigen complexes may be achieved in indirect agglutination test in well trays or by the augmentation with antibody against the species of animal from which antibody against the hapten or antigen has been prepared, effect a direct agglutination on a slide.

15 Claims, No Drawings

IMMUNOLOGICAL TEST PROCEDURE

Immunological test procedures utilizing particles whose agglutination can be macroscopically or microscopically detected are well known in the profession and have been amply described in the literature, (Kabat and Mayer's, 2nd Ed., Experimental Immunochemistry, Chap. 3, Charles C. Thomas, Publ., Springfield, Ill., U.S.A.).

In its simplest form, particles such as bacterial cells of known strain are suspended in a suitable fluid such as a buffer salts solution and then mixed with a suitable volume of suspect serum which might contain antibodies against these cells; the test being performed usually on a glass slide. If the antibodies are present, they will react with specific surface antigens on these cells and thereby cause an agglutination which is usually readily visible macroscopically. Such agglutination tests have been developed, for example, for strains of Salmonella (E. Van Oye, The World Problem of Salmonellosis, Dr. W. Junk, Publ., Hague, Netherlands, 1964).

In the event that the antigen and antibody may be soluble but it is still desirable for reasons of simplicity, speed, or ease of reading the test procedure, to employ an agglutination test, then it has been customary to absorb or otherwise couple the antigen onto the surface of small particles the entirety of which is then reacted with the appropriate antibody resulting in agglutination. Various particles have been used for these purposes and include red blood cells (Middlebrook, G. and Dubos, R., J. Exper. Med., 1948, 88:521: Nater, E., Bact. Rev., 1956, 20:166: Boyden, S. V., J. Exper. Med., 1951, 93:107; Stavitsky, A. B., J. Immunol., 1954, 72;360, 368), collodion particles (Cannon, P. R. and Marshall, C. E., J. Immunol., 1940, 38:365), bentonite particles (Bozicevich, J., Tobie, J. E., Thomas, E. H., Hoyem, H. M. & Ward, S. B. A rapid flocculation test for the diagnosis of Trichinosis. Publ. Hlth. Rep. (Wash.) 66, 806–814), latex particles (Singer, J. M. and Plotz, C. M., Am. J. Med., 1956, 21:888, 893), ion exchange resin, glass, and many others.

In the use of such particles as described above and cited in the literature, the antigen may be absorbed onto the surface of the cell, which is frequently the case with the use of formalinized tanned cells or with latex particles, or may be co-valently bonded to the particle which has the advantage in that the antigen will not readily undergo desorption from the surface of the particle and thereby make inoperative the test procedure for the purpose for which it was intended. Since most antigens are macromolecules, e.g., proteins, it has been customary to use red blood cells for the preparation of such co-valently bonded particles because covalent bonding can readily be performed between the proteins of the surface of a red blood cell and the antigen. One procedure utilizes diazotization in which the aromatic amino groups of the protein on the red blood cells are co-valently bonded to the amino groups of the protein of the antigen (Landsteiner, K., The Specificity of Serological Reactions, Harvard Univ. Press, Cambridge, Mass., 1945). Other methods can utilize a procedure of peptide bond formation utilizing reagents such as carbodiimides which couple carboxylic acid groups to amino groups (Kabat, E. A., Structural Concepts in Immunology and Immunochemistry, Holt, Rinehart and Winston, Inc., New York, 1968.

If an antigen against which antibodies are to react is a weak one or if it is a simple chemical substance (hapten), then the antibodies reacting with such an antigen or a hapten absorbed onto the surface of a red blood cell, or even if co-valently bonded to the cell, will usually not cause direct agglutination. Consequently, a hemagglutination-inhibition or indirect agglutination test may be performed. Such tests are well known in the profession and have been amply described in the literature (Kabat and Mayer, ibid). We shall be using the term hapten in its general sense as describing simple chemical substances which may be determinants of antigenic specificity but must be conjugated to immunogens such as proteins in order to elaborate antibodies in man or animals and/or are usually coupled to suspended particles for their use in an agglutination or passive agglutination test when such determinant groups of haptens are reacted with appropriate antibodies in vitro. The term is also being used here to refer to substances which may be other than simple chemicals such as certain polysaccharides or low molecular weight polysaccharides which in themselves are not antigenic or may be weakly antigenic but whose antigenicity is significantly enhanced when coupled to a protein carrier for injection into man or animals for the elaboration of antibodies specific for such antigens that are weakly antigenic. Again, such weakly antigenic substances may be coupled to particles such as red blood cells for use in an agglutination or passive agglutination test.

It is to be noted that a usual procedure, if not often times a necessary one, for coupling a hapten to the surface of a red blood cell utilizes a binding of the hapten to a protein followed by the binding of the protein carrying the hapten to the surface of the red blood cell. The frequent necessity for this procedure may be attributed to two principal factors:

The reaction between an antibody and a hapten (or antigen) results as a function of the similarity in the chemical structure of the hapten (or antigen) with which the antibody is reacting and the hapten (or antigen) which was utilized for injection into an animal which elaborated these antibodies. Not only the chemical structure per se of the hapten (or antigen) but also the spacial configuration both of the antibody and the hapten (or antigen) with which it is to react are specific for binding between antibody and the hapten (or antigen) to take place. The surface of a cell such as a red blood cell or bacterial cell is composed of inumerable macromolecules which may spacially interfere, due to steric hindrance, with the binding between an antibody and a hapten (or antigen) adsorbed onto the surface of such a cell or even co-valently coupled to it. This steric interference is frequently innumerable by the hapten or other antigen first being coupled to a protein such as for example, bovine serum albumin (BSA). Such procedures have been described in the literature (Adler, F. L. and Liu, Chi-Tan, Detection of Morphine by Hemagglutination Inhibition, J. of Immunology, 106:1684, 1971). It is significant to note that the coupling of a hapten to a macromolecule such as bovine serum albumin is performed whether this complex is to be adsorbed or co-valently coupled to a red blood cell, in order to permit its use in a hemagglutination inhibition test or whether the hapten-BSA complex is utilized as an antigen for injection into suitable animals for the development of antibodies that will react with the hapten contained on the BSA or other macromolecule.

Red blood cells have been extensively used as particulate carriers of haptens or antigens because of the advantages of relative homogeneity of particle size and a suitable proteinaceous surface to which chemical binding of haptens or antigens can take place. Their use, however, has some serious disadvantages:

1. They are highly susceptible to lysis requiring laborious procedures for washing, suspending, and buffering.

2. The procedures for co-valently bonding any haptens or antigens to unpreserved red blood cells must be very mild to avoid their lysis.

3. The receptivity of the surface of the red blood cells for the coupling of haptens or other antigens to its surface may vary greatly depending upon the species of the animal from which the blood is taken and oftentimes from time to time with the same animal from which the blood is taken depending upon various conditions of the state of health of the animal, age of the animal, etc.

4. Another serious defect has to do with the fact that the red blood cells are not stable except for relatively short periods of time and have to be preserved in order to increase their shelf life.

Such preservation procedures are well known and have been reported in the literature. However, even the preservation of red blood cells do not completely preserve the particle for very extended periods of time. The many reports of methods to preserve red blood cells is indicative of the magnitude of work that has been devoted in an attempt to resolve this particular problem: (Ling, N. R., British Journal Hemat., 7:299, 1961; Hirata, A. A. and Brandriss, M. W., Passive Hemagglutination Procedures for Protein and Polysaccharide Antigens Using Erythrocytes Stabilized by Aldehydes, J. of Immunol., 100:641, 1968; Cole, L. R. and Farrell, V. R., A Method for Coupling Protein Antigen to Erythrocytes I. Description of Method. J. of Exper. Medicine, 102:631, 1955; Fulthorpe, A. J., J. Hyg., 55:382, 1957; Ingraham, J. S., Proc. Soc. Exp. Biol. (N.Y.), 99:452, 1958; Weinbach, von R., Schweiz. Z. allg. Path. Bakt., 22:1, 1959; Csizmas, L. Proc. Soc. Exp. Biol. (N.Y.), 103:157, 1960).

An additional problem in performing an agglutination test in which a hapten is the substance to be detected, has to do with the fact that the test is essentially an inhibition test. In such a test, a specimen possibly containing a hapten or antigen to be detected, is reacted for a few minutes with an antibody specific for such hapten or antigen. Particles such as red blood cells which have adsorbed or coupled to their surface the same hapten or antigen as is being detected are then added in order to affect a reaction with the antibody that would be free if the hapten or antigen were absent from the specimen being examined. In such a case the antibody would then react with the hapten or antigens adsorbed or coupled to the cell particles causing them to agglomerate and form a suspended dispersed phase because of this agglomeration whereas cells containing a hapten or antigen which does not react with free antibody, as would occur if the antigen or hapten were present in the specimen being tested would then freely settle to the bottom of a welled tray or tube and collect in a small pellet which is easily discernable from the suspended cells. Such hemagglutination inhibition reactions in which cells are used have been reported in the literature (Adler, F., and Liu, C., J. Immunol., 1971, 106:1684; Adler, F., Liu, C., and Catlin, D., Clin. Immunol. & Immunopathol., 1972, 1:53)

It would be far more desirable and saving in time and labor if the detection of agglutination in which haptens and weak antigens are employed could be achieved in a shorter period of time and with less costly procedures. The invention described herein has succeeded in resolving many of the deficiencies cited above for agglutination tests performed with haptens and may be described as follows:

The role that the particles play, to which a hapten or antigen is adsorbed or otherwise bonded, whether it be red blood cells, latex particles, or similar particles described above, is to provide a macroscopic particulate dispersion which when subjected to antiserum reacting with the antigens or haptens contained hereon, will form agglomerates that are readily discernible macroscopically. If haptens or antigens were to be bound to a soluble protein, which protein could then be suitably aggregated into a particulate suspension, then it would not be necessary to go through the procedure of coupling the soluble protein-hapten (or antigen) complex to a particle such as a red blood cell nor the additional labor made necessary by the use of red blood cells or other particles in agglutination procedures.

Agglomeration of a hapten-macromolecule or antigen-macromolecule to form particles which could be used in an immunological agglutination test system would have a unique advantage over particles currently utilized for such immunological agglutination systems in which the haptens or antigens are either directly or through a carrier protein adsorbed or covalently bonded onto the surface of such particles. Thus, such particles would lose any of their utility for the purpose for which they are designed when the haptens and/or antigens contained on their surface should fall off either for reasons of long-time storge or as a natural consequence of the instability of the binding between the hapten (antigen) and the surface of the particle. In the invention described herein the removal of a surface coat from a hapten-carrier protein agglomerate or antigen-protein carrier agglomerate only bares a new surface containing the same determinate groups that are necessary for the immunological specificity of such agglomerates and thus would not impair the usefulness of particles made in the manner described herein as a result of long-time storage on exposure to conditions which may remove a portion or all of the surface of such sensitized particles.

A general flow sheet of 'prior-art' technology compared to one type of the novelty described herein follows:

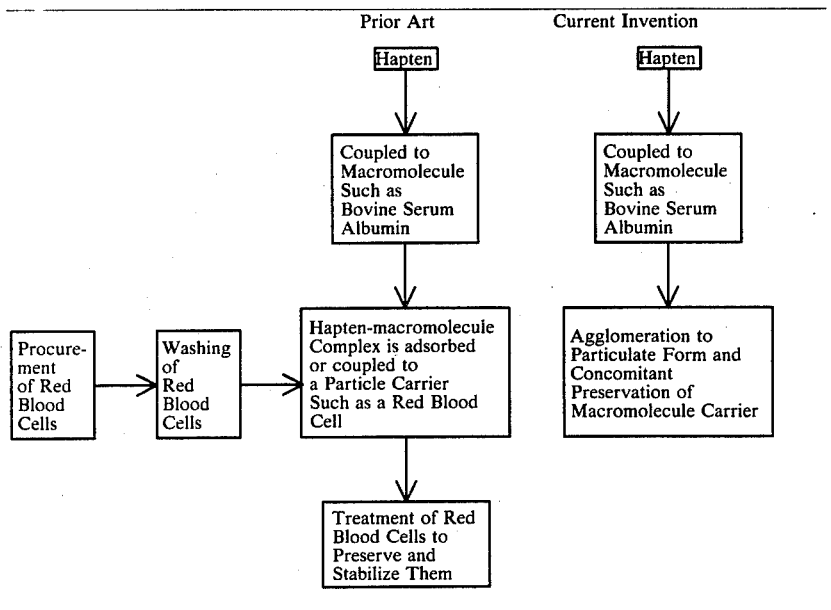

One novelty therefore of the invention described herein is the co-valent bonding of a hapten to a soluble protein carrier which is then rendered particulate, so obviating the necessity of adsorbing or co-valent bonding of such a carrier to a red blood cell or other discrete particle.

Another novelty of the invention described herein is the method of rendering particulate a soluble protein carrier to which a hapten may then be co-valently bonded for the purpose of permitting the observation of agglutination or the lack of it in the presence of specific antibodies.

Another novelty of the invention described herein is the method of augmenting a reaction of an antiserum having antibody activity against a hapten coupled to a protein carrier rendered particulate in order to result in a readily discernible agglutination reaction in a reduced period of time.

Other novel features of the invention herein described will become apparent from the specification and examples cited.

EXAMPLE 1

1.0 gm crystalline bovine serum albumin (BSA) was slowly added to 200 ml of 3.1% gluteraldehyde prepared by mixing 12.5 ml of 50% W/W gluteraldehyde with 187.5 ml of distilled water. The bovine serum albumin is slowly added while the gluteraldehyde solution is being vigorously stirred on a magnetic stirrer. This solution is then subjected to mixing in a blender such as a Waring Blender at high speed for 3 minutes and then refrigerated overnight. After overnight refrigeration the particulate suspension which has formed is spun in a refrigerated centrifuge at 2500 rpm for 30 minutes at 5° C and supernatant discarded. The particles are resuspended in distilled water and respun in the centrifuge under the same conditions, this procedure being repeated a total of three times.

After this washing with water the particles are then resuspended in 65 ml of a phosphate buffer solution at pH 7.3 containing 1% normal rabbit serum (NRS 100) to result in a final concentration of 10 mg BSA per ml. In order to determine that the BSA had not been immunologically denatured in the blending operation, the particulate suspension of BSA prepared as above was reacted with antiserum prepared in sheep against bovine serum albumin. By mixing on a slide one drop of a suspension of aggregated, washed BSA prepared as above with one drop of sheep anti-BSA serum, which serum was diluted serially from 1:100 to 1:400. It is clearly shown (see following table) that direct agglutination took place on the slide at all dilutions whereas control tests in which the antiserum was replaced by phosphate buffer solution pH 7.3 buffer containing 1% normal rabbit serum (NRS 100) resulted in no agglutination.

REACTION OF SHEEP ANTI-BSA SERUM
WITH AGGREGATE SUSPENSIONS OF BOVINE SERUM
ALBUMIN

| REAGENT[1] | VOLUME ADDED (ml)[2] | | | |
|---|---|---|---|---|
| Sheep Anti BSA Serum | | | | |
| diluted[4] 1:100 | .03 | | | |
| diluted 1:200 | | .03 | | |
| diluted 1:400 | | | .03 | |
| NRS 100 | | | | .03 |
| Aggregate Suspension of Bovine Serum Albumin 4 | .03 | .03 | .03 | .03 |
| Results of Slide Test[3] | + | + | + | − |

[1] Abbreviations where used have been cited in text.
[2] Added by calibrated dropping dispenser in which 1 drop = 0.025 ml.
[3] (+) indicates particles agglutinated, (−) no agglutination or trace of agglutination.
[4] All suspensins and dilutions made in NRS 100.

The aggregated BSA, prior to coupling to a hapten or an antigen, was spun in a refrigerated centrifuge at 2500 rpm for 10 minutes at 5° C and resuspended in distilled water. Fifty milliliters of such an aggregated BSA suspension of particles containing 10 mg of BSA per ml is added to 40 ml of carboxymethylmorphine (CMM) which solution contains 10 mg per ml of the CMM. The pH was adjusted to 5.5 and to this mixture is added 400 mg of 1-ethyl-3-(3-dimethylamino-propyl) carbodiimide; this entire mixture is then left to incubate overnight at room temperature.

Following overnight incubation the reaction mixture was spun at 2500 rpm for 10–15 minutes at 5° C and the aggregated bovine serum albumin-carboxymethylmorphine (CMM-BSA) particles resuspended in phosphate buffer 7.3; this spinning and washing operation being repeated approximately 5-7 times to insure that all of the excess carbodiimide was washed away.

The CMM-BSA particles are then resuspended in NRS 100. In order to demonstrate that the aggregated BSA particles now contain CMM and can be utilized in a reaction for the determination of morphine in body fluids, an indirect agglutination test is performed essentially using the method as outlined by Adler and his co-workers (Ibid.) except that the aggregated CMM-BSA particles prepared as above is substituted for the formalinized, tanned, and sensitized sheep red blood cells.

A volume of 0.025 ml of a sample containing morphine at a concentration of 15 nanograms (ng) per ml is placed into each of 4 wells. In another 4 wells a sample known to be free of morphine is dropped at the same time and at the same volume. Into two of the wells containing the morphine sample and into two of the wells containing the sample free of morphine, 0.025 ml of a concentration of antimorphine antiserum, suitably diluted so as to be inhibited by a quantity of morphine equal to 50 ng per ml. Into the other 4 wells is placed 0.025 ml of NRS 100 Diluent which will represent the controls.

After 5 minutes and into all wells, are placed 0.05 ml of the aggregate suspension of CMM-BSA. The nicrotiter tray containing the wells is rotated for ½ minute to insure suitable dispersion of the particles and after 1½-2 hours the results may be read. The results are shown in the following table in which (−) indicates the presence of agglutination (absence of morphine), i.e., antibody was not neutralized by morphine and was therefore available to react with the CMM-BSA aggregate particles which remain suspended and (+) indicates that no agglutination took place, i.e., morphine was present in the specimen and bound the available antibody, in which case the aggregate CMM-BSA particles settle to the bottom of the well of a titer tray in approximately 1½-2 hours.

AGGLUTINATION INHIBITION TEST USING AGGREGATED CMM-BSA PARTICLES

|  | Sheep Anti CMM Antiserum .025 ml per drop + .05 ml of aggregated CMM-BSA | Controls Diluent (No Morphine) .025 ml + .06 ml of aggregated CMM-BSA |
|---|---|---|
| Sample containing Morphine (50 ng/ml) .025 ml | + | + |
| Sample free of Morphine .025 ml | − | + |

EXAMPLE 2

Aggregated particles of CMM-BSA prepared as indicated above in Example 1 were suspended in NRS 100. The concentration of the CMM-BSA particles was determined by centrifuging in a calibrated tube and 0.8 ml of such aggregate particles calculated as packed material was suspended in 100 ml NRS 100.

One drop of the aggregated CMM-BSA suspension was placed on a glass slide followed by one drop of sheep anticarboxymethylmorphine serum appropriately diluted. The two drops were mixed by tilting the slide back and forth and, after 3 minutes, examination indicated that no agglutination of the particles had taken place. To this mixture was then added one drop of rabbit anti-sheep IgG serum which was thoroughly mixed with the previous suspension and the glass slide tilted back and forth for approximately 3-5 minutes after which time a clear agglutination reaction appeared. By performing the experiments indicated in the following table with suitable controls, it was clearly shown that such augmented treatment of the aggregate suspension of CMM-BSA particles would result in a direct agglutination in an overall time of approximately 12 minutes.

AUGMENTED AGGLUTINATION OF AGGREGATE CMM-BSA PARTICLES

| REAGENT[1] | VOLUME ADDED (ml)[2] | | | | | | | | |
|---|---|---|---|---|---|---|---|---|---|
| HRS 100 | .03 | 0.3 | .03 | .03 | .03 |  |  | .03 | .03 |
| Aggregated CMM-BSA particles (.75% suspension) | .03 | .03 | .03 | .03 | .03 | .03 | .03 | .03 | .03 |
| Sheep Anti CMM serim | .03 | .03 | .03 | .03 | .03 | .03 | .03 | .03 |  |
| Rabbit Anti-Sheep IgG Serum (concentrated) | .03 |  |  |  |  |  |  |  |  |
| diluted 2 times |  | .03 |  |  |  |  |  |  |  |
| 10 diluted 4 times |  |  | .03 |  |  | .03 | .03 |  | .03 |
| diluted 8 times |  |  |  | .03 |  |  |  |  |  |
| diluted 16 times |  |  |  |  | .03 |  |  |  |  |
| Morphine Solution 50 ng/ml |  |  |  |  |  | .03 |  | .03 | .03 |
| 100 ng/ml |  |  |  |  |  |  | .03 |  |  |
| Results[3] | − | + | + | + | − | − | − | − | − |

[1] Abbreviations where used have been cited in text.
[2] Added by calibrated dropping dispenser in which 1 drop = 0.025 ml.
[3] In all cases 5 minutes elapsed between the addition of antimorphine serum and the aggregated CMM-BSA particles; a period of 3 minutes elapsed between the adition of the particle suspension and the addition of rabbit anti-sheep IgG antiserum. (+) indicates particles agglutinated, (−) no agglutination or trace of agglutination.

It has also been found feasible to co-valently couple a hapten or antigen to a protein in solution and then institute the reactions resulting in aggregation of the protein carrying the hapten or antigen which aggregates retain antigenic activity for their use in an indirect or in an augmented agglutination test which procedures can be demonstrated by the following experiments.

EXAMPLE 3

250 mg of No. 1 grade bovine serum albumin was dissolved in 25 ml of distilled water and 200 mg of carboxymethylmorphine dissolved in 20 ml of distilled water was added to it. The pH was adjusted to 5.5 after which 200 mg of the carbodiimide in 5 ml of distilled water was added. This mixture was incubated overnight at room temperature. Dialysis against 4 liters of distilled water was performed for 3 days with daily changes of distilled water. The concentration, calculated as bovine serum albumin, of the bovine serum albumin-carboxymethylmorphine complex was diluted with distilled water to a concentration of 1 mg per ml. A test was first performed in order to determine that active hapten-coupled BSA protein had been achieved by sensitizing the CMM-BSA complex to freshly-washed sheep red blood cells as follows:

3.6 ml of the CMM-BSA complex at a concentration of 1 mg/ml (calculated as protein) was added to 2.8 ml of phosphate pH 7.3 buffer and 3.2 ml of a 5% suspension of washed sheep red blood cells plus 1.6 ml of 1:15 diluted bis diazabenzidine while the entire mixture was thoroughly stirred and kept at 0° C temperature. After 5 minutes, the red blood cell suspension was centrifuged, resuspended in fresh phosphate buffer pH 7.3 followed by 3 such washings. The final cell pellet was resuspended in phosphate buffer pH 7.3 containing 1% normal rabbit serum (NRS 100).

Utilizing a microtiter-type tray and serial dilutions of antiserum which was prepared in sheep against CMM-BSA antigen but absorbed with bovine serum albumin to absorb out the anti-BSA antiserum, a serial dilution of such antiserum from 1:200 to 1:25,600 was prepared. The following table indicates the scope of the experimental design and the results.

| ANTIBODY DILUTION | EXAMINATION OF CARBOXYMETHYLMORPHINE BOVINE SERUM ALBUMIN SENSITIZED SHEEP RED BLOOD CELLS AGAINST SHEEP ANTI-CARBOXYMETHYLMORPHINE ANTISERUM[1] | | | | | | | | |
|---|---|---|---|---|---|---|---|---|---|
|  | 1:200 | 1:400 | 1:800 | 1:1600 | 1:3200 | 1:6400 | 1:12800 | 1:25600 | Control |
| Zero Morphine | − | − | − | − | − | − | + | + | + |
| 10 ng morphine/ ml of urine | − | − | − | − | + | + | + | + | + |
| 50 ng/ ml of urine | − | − | + | + | + | + | + | + | + |

[1]Where zero morphine is used, 1 drop of phosphate buffer pH 7.3 containing 1% normal rabbit serum was placed into each well. One drop each of the 10 ng/cc solution and 50 ng/cc solution was placed in their respective rows. One drop each of the serial dilutions of the antiserum placed in ther vertical columns except for the control which did not contain antiserum but received a drop of phosphate buffer 7.3 containing 1% of normal rabbit serum albumin.
After 10 minutes, to permit the antiserum and morphine to react, 2 drops of a cell suspension sensitized with carboxymethylmorphin-bovine serum albumin prepared as above was added to each of the wells. The tray was gently rotated and after 2 hours was read for agglutination.
(−) indicates that agglutination of the antiserum in the cells took place, and
(+) indicates that the cell pellet settled and that no antiserum was available to react with the cells.

The results clearly showed that the prepared carboxymethylmorphine-bovine serum albumin was reacting with the anti-carboxymethylmorphine antiserum thus causing agglutination of the red blood cells to which the CMM-BSA was coupled.

20 ml of the carboxymethylmorphine-bovine serum albumin as described above, containing 1 mg of protein per ml, was placed in a 100 ml Erlenmeyer flask with a small magnetic stirrer and, while stirring took place, 0.5 ml of 50% gluteraldehyde solution was slowly added to the solution. The pH was adjusted to 5.3 and the beaker was stored in the refrigerator overnight.

After overnight incubation a precipitate had occurred which was then dispersed into fine particles with a tissue culture grinder and the particles tested in order to determine that they would bind anti-carboxymethylmorphine antiserum.

The experiments were performed exactly as indicated in Example I and the results were the same as shown for the table entitled AGGLUTINATION INHIBITION TEST USING AGGREGATED CMM-BSA PARTICLES.

It has thus been shown that the preparation of a hapten, co-valently bonded to a soluble macromolecule, followed by aggregation into insoluble particles could be utilized in a diagnostic test procedure in the same way as would be effected by the aggregation of a soluble macromolecule into a particulate state followed by the co-valent bonding to it of a hapten or antigen.

Although the examples here given for the protein carrier to which the hapten or antigen may be co-valently coupled has been bovine serum albumin, it is clear that macromolecules other than albumin may be utilized without deviating from the principles of the invention described herein.

The examples herein cited utilize carboxymethylmorphine as a small molecule (hapten) but these experiments have been repeated with other haptens such as 4-dimethylamino-2,2-diphenylpentanoic acid, ecgonine, and 5-ethyl-5-(1 carboxy-n-propyl) barbituric acid where these haptens were co-valently bonded to carrier proteins and the contents then agglomerated using the same method as employed for carboxymethylmorphine and having essentially the same results when such particles were used in agglutination-inhibition tests.

Although gluteraldehyde has been utilized in the experiments described herein for agglomerating macromolecules such as proteins to which haptens may or may not have been co-valently bonded or adsorbed, such agglomeration for the purpose of providing a particle that can be utilized in an immunological agglutination reaction may not be restricted to macromolecules since smaller molecules, and even amino acids, would lend themselves to cross-linking with gluteraldehyde with a resulting particulate state formed therefrom (Avrameas, S. and Ternynck, T., The Cross-Linking of Proteins with Glutaraldehyde and its Use for the Preparation of Immunoadsorbents, Immunochemistry, 6:53–66, 1969) without deviating from the novelty of of the principles described herein.

Although glutaraldehyde has been principally described herein as the cross-linking agent to produce macro particles from soluble chemical agents, it is clear that other reagents may be utilized for exactly the same purpose without deviating from the novelty of the invention herein described; such as ethychloroformate and paraformaldehydes to cite a few examples.

Thus, although most of the examples contained herein have utilized bovine serum albumin as the soluble carrier protein to demonstrate agglomeration by glutaraldehyde and similar cross-linking agents, innumerable other proteins necessarily having amino acid determinant groups capable of being cross-linked by an aldehyde group can be utilized for such purpose without deviating from the novelty of the invention described herein; the purpose of the protein being to provide a cross-linking agent so resulting in agglomerates that become particulate and to which haptens and antigens can readily be co-valently bonded or otherwise fixed.

I claim:

1. The method of aggregating aqueous soluble macromolecules containing co-valently linked immunologically reactive functional groups which comprises cross-linking the macromolecules with a cross-linking agent to result in aqueous insoluble particles which particles can be utilized in an immunological agglutination reaction with antibodies specific for the reactive functional groups.

2. The method of claim 1 in which cross-linking is achieved with gluteraldehyde.

3. The method of claim 2 in which the molecule carrying the functional group is a serum albumin.

4. The method of claim 3 in which the albumin is bovine.

5. The method of claim 3 in which the molecule carrying the functional group is a polypeptide.

6. The method of claim 3 in which the molecule carrying the functional group is an amino acid.

7. An aqueous insoluble aggregate particle comprising macromolecules each containing a co-valently linked immunologically reactive functional group in which the macromolecules are joined by a cross-linking reagent thereby resulting in the entrapment of the functional groups within the aggregate particle which particle can be utilized in an immunological agglutination reaction with antibodies specific for the functional group.

8. An aqueous insoluble aggregate particle as described in claim 7 in which the particle does not derive from nor utilize in part or in whole a red blood cell or any other intact particle.

9. The aggregate particle as described in claim 7 in which the macromolecule to which the functional group is co-valently bonded is a polypeptide.

10. The aggregate particle as described in claim 7 in which the macromolecule carrying the immunologically reactive functional group is bovine serum albumin.

11. The aggregate particle as described in claim 7 in which the macromolecule is cross-linked with gluteraldehyde.

12. The aggregate particle as described in claim 7 in which the co-valently linked immunologically reactive functional group is a hapten.

13. An aqueous insoluble aggregate particle comprising amino acids each containing a co-valently linked immunologically reactive functional group in which the amino acids are joined by a cross-linking reagent thereby resulting in the entrapment of the functional groups within the aggregate particle which particle can be utilized in an immunological agglutination reaction with antibodies specific for the functional group.

14. The aggregate particle as described in claim 13 in which cross-linking is achieved with gluteraldehyde.

15. The aqueous insoluble aggregate particle as described in claim 13 in which the co-valently linked immunologically reactive functional group is hapten.

* * * * *